United States Patent [19]

Haefele et al.

[11] Patent Number: 4,996,049

[45] Date of Patent: Feb. 26, 1991

[54] BIOLOGICAL CONTROL OF CORN SEED ROT AND SEEDLING BLIGHT

[75] Inventors: Douglas M. Haefele, Newton; Jonathan C. Lamptey; Joseph L. Marlow, both of West Des Moines, all of Iowa

[73] Assignee: Pioneer Hi-Bred International, Inc., Des Moines, Iowa

[21] Appl. No.: 286,032

[22] Filed: Dec. 19, 1988

[51] Int. Cl.$^5$ .................. C12R 1/425; C12R 1/39; A01N 63/00

[52] U.S. Cl. .................. 424/93; 435/253.3; 435/252.1

[58] Field of Search ............ 424/93; 435/253, 253.3, 435/252.1

[56] References Cited

U.S. PATENT DOCUMENTS 4,647,533 3/1987 Weller et al. .................. 435/29

FOREIGN PATENT DOCUMENTS

PCT/US87/-
01645 7/1987 PCT Int'l Appl. .

OTHER PUBLICATIONS

Stutz et al., 1986, Phytopathology 76(2): 181–185, (Abstract).

Weller et al., 1986, Can. J. Plant Pathol. 8(3):328–334 (Abstract).

Cameron et al., "The Mannoprotein of *Saccharomyces Cerevisiae* Is an Effective Bioemulsifier," *Applied and Environmental Microbiolgy*, vol. 54, 1420–1425, (1988).

Cirigliano et al., "Purification and Characterization of Liposan, A Bioemulsifier," *Applied and Environ. Microbiology*, vol. 50, 846–850 (1985).

Cooper et al., "Surface-Active Compounds from Microorganisms," *Advances in Applied Microbiology*, vol. 26, 229–253, (1980).

Howell et al., *Phytopathology*, vol. 70, No. 8, pp. 712–715 (1980).

Sabet, Kommedahl, Burnes, *Phytopathology*, vol. 77, No. 12, p. 1771 (1987).

Kosaric et al., "Microbial Emulsifiers and De-Emulsifiers," Chapter 3i.

Cooper, *Microbiological Sciences*, vol. 3, No. 5, pp. 145–149 (1986).

Margaritis et al., *Biotechnology and Bioengineering*, vol. XXI, pp. 1151–1162, 1979.

Parkinson, *Biotech Advs.*, vol. 3, pp. 65–83 (1985).

Persson et al., *Appl. Microbiolo Biotechnol*, 29:1–4 (1988).

Xu and Gross, *The American Phytopathological Society*, vol. 76, No. 4, 423–430 (1986).

*Primary Examiner*—Margaret Moskowitz
*Assistant Examiner*—Keith C. Furman
*Attorney, Agent, or Firm*—Zarley, McKee, Thomte, Voorhees & Sease

[57] ABSTRACT

Treating composition and method for biological control of corn seed rots and seedling blights. The composition comprises a culture of emulsifier and surfactant producing bacteria selected from the strains of 6519EO1, 6133DO2, 6109DO1, and their respective genetic equivalents and a carrier. The composition is applied to seeds or the aqueous media surrounding seeds in plant growth media to prevent corn seed rot and seedling blight.

6 Claims, No Drawings

BIOLOGICAL CONTROL OF CORN SEED ROT AND SEEDLING BLIGHT

BACKGROUND OF THE INVENTION

This invention relates to a means for biological control of certain soil borne plant pathogens. Biological control is defined as pathogen control by use of a second organism. The mechanisms of biological control are quite diverse. In some instances the control is caused by production of certain chemicals by the biological organism, with the chemicals being inhibitory. In other instances, there is competition for space with the control organism occupying space, and consuming nutrients which inhibit the organism to be controlled. In further instances it may be nothing more than competition for chemical nutrients. In any event, the concept of biological control when used herein is as defined in this paragraph.

The biological control mechanism of this invention is especially designed for control of seed corn rot and corn seedling blight. It is possible that the control method of the present invention may be used for certain other plants which suffer from similar diseases caused by high moisture content in the growing media at planting time. Thus, the invention is not limited to control of corn seed rot and seedling blight, but instead is a method of controlling any types of "damping off" or "root rot" that crops such as corn, alfalfa, soybeans, etc. are known to have.

In the typical progress of corn seed rot, and seedling blight the symptoms occur early in the spring soon after planting or seed germination in a disease conducive environment. Often the seedling will be destroyed, the leaves yellow and wilt, the roots rot and fail to properly develop, and the plant is significantly impaired. It may even die. This disease is especially common when there is not only high moisture during spring planting season, but also colder temperatures.

Currently, the best known methods for treatment are chemical treatment with fungicides such as Captan. However, because of recent environmental concerns it is especially desirable to eliminate the use of potentially environmentally hazardous fungicides, such as Captan.

There is, therefore, a continuing high level of interest in developing other means for treating bacteria and fungi known to cause corn seed rot and seedling blight, especially those caused by Pythium Spp. and *Fusarium graminearum*. These are perhaps two of the most common species causing corn seed rot and seedling blight.

It is a primary objective of the present invention to provide a method of biological control of corn seed rot and seedling blight.

Another objective of the present invention is to provide a treating composition of inoculum for control of corn seed rot and seedling blight, which comprises a protection effective amount of a bacteria which produces bioemulsifiers and/or biosurfactants. It is selected from the group consisting of strains 6519E01, 6133D02, 6109D01 and their respective genetic equivalents, combined with a satisfactory carrier.

Another objective of the present invention is to provide a method of biological control which comprises placing the treating composition on the seed, or adjacent the seed in a growing medium, to protect said seed during its critical time periods just prior to and just after germination. Protection is provided from hazards of blight caused by *Pythium Spp.* and *Fusarium graminearum*, etc.

The method and means of accomplishing the objectives of the present invention will become apparent from the detailed description which will follow hereinafter.

SUMMARY OF THE INVENTION

The cultures of the present invention are used for biological control by a bioemulsifier and biosurfactant producing bacteria. They are selected from the group consisting of strains 6519E01, 6133D02, 6109D01 and their respective genetic equivalents, as well as mixtures thereof. It is believed these strains are active in part because they produce bioemulsifiers and/or biosurfactants. These may interact with the aqueous media to potentially transport away from the seed, or the seedling after germination, aqueous media containing pathogens such as Pythium Spp. and *Fusarium graminearum*, which are known to induce corn seed rot and seedling blight.

DETAILED DESCRIPTION OF THE INVENTION

The bacterial strains selected for use in preparing the biological control systems of the present invention were selected after screening about 5000 strains from various growing media. Only the three strains of the present invention, and their genetic equivalents or mutants thereof, exhibit the unusual property of successful biological control of corn seed rots and seeding blights.

The bacterial strains of the present invention have been code designated as strains 6519E01, 6133D02 and 6109D01. These strains have been deposited at the American Type Culture Collection, Rockville, Md., and have been assigned ATTC Accession Nos. 53860, 53859 and 53858, respectively. The term genetic equivalents as used herein is to be understood to mean not only the precise strains of the present invention, but mutants thereof, or genetically altered bacteria which nevertheless have the common identifying characteristic of the present invention, i.e. they produce biosurfactants and/or bioemulsifiers which behave in the same or similar or equivalent manner which may be important to providing effective biological control of pathogens causing corn seed rot and corn seed blight.

The three bacterial strains selected involve two members of the genus Pseudomonas, and a third bacteria from the genus Serratia. These may be described in the following manner.

Organisms (6519E01 and 6133D02) are gram negative, produce white colonies on yeast-dextrose calcium carbonate agar, and are fluorescent on King's medium B placing them in the genus Pseudomonas. They were positive in oxidase and arginine dihydrolase tests, positive in gelatinase tests, were able to grow at 5° C., and unable to grow at 41° C. These results place them in the *Pseudomonas fluorescens* group.

*Pseudomonas fluorescens* (6519E01) is an isolate which most closely resembles *P. fluorescens biovar* V, although it differs from most biovar V strains in the utilization of D-alanine. It is variable in the use of this carbon source and strains of biovar V are by definition unable to utilize this carbon source.

*Pseudomonas fluorescens biovar* I (6133D02) is an isolate able to utilize sucrose and D-alanine as carbon sources and produces levan. It is unable to reduce nitrate and cannot utilize L-tartrate as a sole carbon source. By these criteria it fits the biovar one classification.

The third organism (6109D01) is of the genus Serratia and is a member of the family Enterobacteriaceae. Essential characteristics of the genus Serratia include the production of extracellular gelatinase, lecithinase, and DNase. Extensive carbon source utilization tests were used to identify strains of the genus serratia to species. Some differential tests might include: inability to grow on adonitol or erythritol as sole carbon sources, positive for growth at 5° C., and negative for growth at 40° C. Identification to species was carried out in accordance with the work of Grimont and Grimont. Strain 6109D01 is *Serratia plymuthica*.

From time to time it is referred to herein as a biologically pure or substantially pure culture of these above referred-to strains. This is intended to refer to a culture which contains no other bacterial species in quantities sufficient that they interfere with the pathogen-treating effectiveness of the strains above referred to. The term "seed treating effective amount" or "protecting amount" as used herein refers to an amount of the biological pathogen control composition which is sufficient to produce effective field treatment to provide a noticeable field decrease of corn seed rot and corn seed blight.

The common denominator for each of the referred to strains herein are that each produce biosurfactants. The term "biosurfactants" as used herein is intended to include both emulsifiers and surfactants. Generally speaking, each of the three strains, their genetic equivalents, or their mutants are known to reduce the surface tension of an aqueous medium from its normal level of about 72.5 dynes/cm downwardly as much as 40%, preferably within the range of at least 40% to 80% and especially from about 50% to about 75% surface tension reduction. Generally, all of the organisms useful for biological control in this invention will successfully reduce the surface tension of water from its normal 72.5 dynes/cm down to 40 dynes/cm and at least in one instance with respect to strain 6519E01, will reduce the surface tension down to at least 20 dynes/cm.

It is not known precisely why the biological controls of the present invention work. While applicants do not wish to be bound by a theory of operability, it is believed that they work in part because of the characteristic nature of each of the organisms of producing biosurfactants. The biosurfactants may result in pathogen control by a number of different mechanisms. One of those mechanisms may well be to aid in the redistribution of soil borne plant pathogens on a natural basis. Put another way, the biological control agents of the invention when either on the seed or adjacent thereto, produce the biosurfactants which then interact with the aqueous media, aiding in protecting from attacks by soil borne plant pathogens, such as Pythium Spp. and *Fusarium graminearum.* It may also be possible that the biosurfactants are simply potentiating the activity of other protective agents by facilitating dispersal around the seed.

The biological controls may either be applied to the seed or directly applied to the growing medium, but are preferably applied to the seed. They may be applied to the seed by mixing with a suitable carrier, and applying a thin coating on the seed. This can be done by soaking followed by planting of the seed. It can also be done by low water volume spray application. Neither the carrier nor the precise manner of either dry application or soaking application in a liquid medium appears to be critical. Suitable carriers are those which do not inhibit the growth of the bacteria, nor are they harmful to the seed. Generally speaking, suitable carriers may be water and for example aqueous methyl cellulose.

The following examples are offered to further illustrate but not limit the process and composition of the present invention.

EXAMPLE 1

Seeds were coated with bacterial cells grown in specific media as medium composition has been found to influence efficacy. All *Serratia plymuthica* strains were grown in half-strength tryptic soy broth. *P. fluorescens* strain 6133D02 was grown in nutrient broth. *P. fluorescens* strain 6519E01 was grown in potato dextrose broth. Stationary phase cultures were used in all cases. Seed was coated by one of two methods, either high volume coating or low volume coating.

In high volume coating, the Pseudomonas treatments were coated onto seeds by centrifugation and resuspending the cells in approximately 15 mls of culture supernatant for every 125 seeds to be coated. The resulting cell suspension was approximately $5\times10^8$ cfu per ml. Seeds were allowed to soak in this suspension for at least 30 minutes. They were then removed from the cell suspension and dryed in moving air.

In low volume coating, the Serratia treatments were coated onto seed by a similar method except that cells were resuspended into only 1 ml of culture supernatant and applied to 200 seed in a small rotating drum before air drying. This treatment has since been found to be less desirable than the first, at least for some organisms.

Field trials were conducted in the following manner. A randomized complete block design was used at all stations. Four or five replications per entry were used depending on the location.

The field trials were conducted at six sites in the spring of 1988. Algona, Iowa; 1 row plot, 50 seeds per row; planted April 8th. Johnston, Iowa; 1 or 2 row plots, 50 or 100 seed, April 4, 8, 11. Princeton, Ill.; 2 row plot; 25 seed per row; April 12th. Willmar, Minn.; 1 row plot; 50 seed per row; April 19th. Windfall, Ind.; 2 row plot; 50 seed per row; April 12th. York, Neb.; 2 row plot; 50 seed per row; March 29th.

Non-treated seed and seed treated with one of the following were planted using standard agronomic practices: Apron (fungicide), Captan (fungicide), 6109D01, 6109D06, 6171B01, 6120A04, 6133D02, 6519E01±6109D01, or 6509E01. Those organisms not designated as part of the present invention were selected for field test, but were not successful biological controls and are presented here for data comparison only.

All stations measured the standard trait generally referred to as early stand count or seedling emergence. This is simply a numerical count of the number of emerging seedlings. At Johnston station data on biomass production was also collected.

Standard analysis of variance and mean separation tests were carried out on the data from locations showing significant reduction in stand due to fungal disease.

Data was grouped from plots where a significant difference in emergence was found between raw seed and seed treated with any of the chemical fungicides. The raw data from a location were expressed as a fraction of the mean emergence of all treatments within that one location. This variable was called standardized emergence and was used to generate all statistical analyses presented here. Analysis of the non-transformed data set resulted in identical conclusions except that Station and Location were additional sources of significant variability. The normalization by location mean was instituted to reduce variability in the data set due to pooling the data from several stations and locations within a station. The distribution of the new variable was found to approximate a normal distribution.

Analysis of variance showed two significant sources of variability in this data set. They were treatment and the interaction of treatment with the trial site (station). The interaction of trial site and treatment was expected as edaphic, climatic, and environmental factors were all known to influence strain efficacy.

Table 1 presents mean separation for standard emergence at the six locations where fungal disease was present.

TABLE 1
(Multiple Range Test Results)

| Treatment | Standardized Mean Emergence | Duncan Grouping | Plots/Treatment Across All Locations |
|---|---|---|---|
| Apron | 1.09 | A | 25 |
| Captan | 1.08 | A | 25 |
| 6133D02 | 1.04 | AB | 25 |
| 6519E01 + 6109D01 | 1.03 | AB | 25 |
| 6519E01 | 1.01 | BC | 25 |
| 6109E01 | 0.98 | BCD | 25 |
| 6120A04 | 0.97 | BCD | 25 |
| 6109D06 | 0.96 | CD | 25 |
| 6171B01 | 0.93 | D | 25 |
| RAW | 0.93 | D | 25 |

In table 1 the term "Duncan Grouping" refers to a statistical method of data analysis. This is the generally accepted method of analysis for this type of data. Treatment means followed by the same Duncan grouping letter do not differ significantly at the 95% confidence level.

Table 1 shows that across all locations where fungicide treatment significantly increased emergence, treatment of seed with strain 6133D02 or the mix of strains 6519E01 and 6109D01 provided emergence equal to commercial fungicides. Seed treatment with strain 6519E01 alone provided protection significantly better than no treatment.

At the Johnston station above ground biomass production was also measured for treatments 6519E01, 6120A04, 6133D02, and the controls on Pioneer Seed Corn® hybrid 3475. Total biomass production by plants grown from seed treated with 6519E01 (27.0 g) was significantly greater than the total biomass of the non-treated seed (17.9 g) and was equal to that of Captan (22.0 g) and Apron (22.9 g). Strain 6133D02 did not significantly increase total biomass (23.2 g) above the non-treated seed. However, it equaled biomass production by either Captan or Apron treated seed. In addition, the biomass per plant of plants from seed treated with 6519E01 (0.61 g) was significantly greater than the biomass per plant of plants from non-treated seed (0.46 g) or from seed treated with Captan (0.50 g) and was not significantly different from the biomass per plant of plants from seed treated with Apron (0.52 g).

Strain 6519E01 may be able to promote seedling growth as well as prevent attack by fungal pathogens. At the one location where data was collected on above ground biomass production seed treatment with 6519E01 resulted in significantly larger plants as well as significantly higher emergence which equaled the protection provided by chemical fungicides.

EXAMPLE 2

Each of the three strains of the present invention were further analyzed for their characteristic development of biosurfactant and bioemulsifier properties. The data for the surfactant and bioemulsifier characterization studies are presented below.

Emulsification was determined by a modification of the method of Gerson and Zajic: 6 mL of kerosene or vegetable oil and 4 mL of aqueous surfactant, consisting of X mL (0.1 mL:1.0 mL) of whole broth and 4×mL of distilled water, were vigorously vortexed in a test tube for two minutes. If an emulsion formed, the percentage of the total volume occupied by the emulsion was measured with time as a variable. From a plot of log percent emulsion versus time the slope of the straight line was determined and divided into 0.693 to give the half-life of the emulsion in hours.

Each of the bacterial strains of the present invention exhibited either trivial or poor emulsifying properties after fermentation growth times of about 7 hours. However, at times varying from 24 hours upwardly, the bioemulsifier capabilities significantly improved.

The following examples illustrate the biosurfactant emulsion activity of the protective compositions produced by the bacterial strains of the present invention. The tables illustrate the kinetics of decay of emulsion under gravity using the protocol earlier described.

In Table 3 below the organism was *Pseudomonas fluorescens* strain 6519E01 and the growth medium was potatoe dextrose broth (PDB). The fermentation growth time was 48 hours.

TABLE 2

| % Emulsion | Stability Time (hours) |
|---|---|
| 71 | 0 |
| 71 | 1 |
| 69 | 4 |
| 69 | 6 |
| 64 | 24 |
| 63 | 48 |
| 62 | 72 |

In Table 3 below the organism was *Pseudomonas fluorescens* strain 6133D02 and the growth medium was nutrient broth (NB). The fermentation growth time was 40 hours.

TABLE 3

| Stability Time (hours) | % Emulsion | |
|---|---|---|
| | Kerosene | Oil |
| a. Oxygen Level 1 | | |
| 0 | 80 | 70 |
| 1 | 65 | 65 |
| 6 | 63 | 60 |
| 16 | 62 | 57 |
| 24 | 62 | 55 |
| b. Oxygen Level 2 | | |
| 0 | 84 | 64 |
| 1 | 73 | 64 |
| 6 | 70 | 54 |
| 16 | 69 | 53 |
| 24 | 68 | 53 |

In Table 4 below the organism was *Serratia plymuthica* strain 6019D01. The fermentation growth time was 40 hours.

TABLE 4

| % Emulsion | Stability time (hours) |
|---|---|
| a. Oxygen Level 1 | |
| 78 | 0 |
| 76 | 1 |
| 77 | 3 |
| 78 | 24 |
| 78 | 48 |
| 78 | 72 |
| b. Oxygen Level 2 | |
| 78 | 0 |
| 78 | 3 |
| 78 | 5 |
| 76 | 21 |
| 76 | 24 |
| 76 | 48 |
| 76 | 72 |

It can be seen that *P. fluorescens* 6519E01, *P. fluorescens* 6133D02, and *S. plymuthica* 6109D01 all were effective bioemulsifiers. The best surface tension measurements or each of these respective strains from numerous fermentation runs is the following. For *P. fluorescens* 6519E01, 26.8 dynes/cm; for *P. fluorescens* 6133D02, 58 dynes/cm; and for *S. plymuthica* 6109D01, 43 dynes/cm.

It can be seen from the field test data that each of these strains are noticeably effective as successful biological controls for seed corn rot and blight. The biosurfactant data shows they also produce efficient biosurfactants.

We claim:

1. A method of protecting corn plants in a growing medium from seed blight and seed rot, comprising:
   placing in the growth medium in the immediate vicinity of the corn plant a small but plant protecting effective amount of a bacteria which produces emulsifiers and surfactants that can reduce the surface tension of water in the growing media by at least 40%, which are selected from the group consisting of *Pseudomonas fluorescens* strain 6519E01 having an ATCC accession number of 53860, *Pseudomonas fluorescens* strain 6133D02 having an ATCC accession number of 53859, and *Serratia plymuthica* strain 6109D01 having an ATCC accession number of 53858 and the genetic equivalents thereof which provide effective biological control of pathogens causing corn seed rot and corn seed blight and mixtures of said strains.

2. A method of protecting corn plants from seed blight and seed rot caused by seed germination in growth environments conductive to disease, said method comprising:
   applying to the seeds of said corn plant a small but surface tension reducing effective amount of emulsifiers and surfactants or mixtures thereof produced from cultures of bacteria;
   said emulsifiers and surfactants or mixtures thereof being further characterized as those which can reduce the surface tension of an aqueous media by at least 40% and which are further selected from the group consisting of *Pseudomonas fluorescens* strain 6519E01 having an ATCC accession number of 53860, *Pseudomonas fluorescens* strain 6133D02 having an ATCC accession number of 53859, and *Serratia plymuthica* strain 6109D01 having an ATCC accession number of 53858 and the genetic equivalents thereof which provide effective biological control of pathogens causing corn seed rot and corn seed blight and mixtures of said strains.

3. The method of claim 1 wherein the bacteria have the capability of reducing aqueous surface tension by an amount within the range of about 40% to about 80%.

4. The method of claim 5 wherein the surface tension reducing capability for aqueous medium is within the range of about 50% to about 75%.

5. The method of claim 2 wherein the surface tension reducing capability is within the range of about 40% to about 80%.

6. The method of claim 2 wherein the surface tension reducing capability is within the range of about 50% to about 75%.

* * * * *